United States Patent
Fuisz et al.

(10) Patent No.: US 7,824,612 B2
(45) Date of Patent: Nov. 2, 2010

(54) BODILY FLUID ANALYZER, AND SYSTEM INCLUDING SAME AND METHOD FOR PROGRAMMING SAME

(76) Inventors: Richard C. Fuisz, 1127 Langley La., McLean, VA (US) 22101; Joseph M. Fuisz, 1100 Connecticut Ave., NW., Suite 440, Washington, DC (US) 20036

( * ) Notice: Subject to any disclaimer, the term of this patent is extended or adjusted under 35 U.S.C. 154(b) by 0 days.

(21) Appl. No.: 11/790,131

(22) Filed: Apr. 24, 2007

(65) Prior Publication Data
US 2008/0004812 A1    Jan. 3, 2008

Related U.S. Application Data

(60) Provisional application No. 60/794,117, filed on Apr. 24, 2006.

(51) Int. Cl.
*G01N 21/00*     (2006.01)
*G01N 35/02*     (2006.01)
*A61B 5/00*       (2006.01)
*G01N 15/06*     (2006.01)

(52) U.S. Cl. .............................. 422/62; 422/61; 422/63; 422/64; 422/65; 422/67; 422/68.1; 436/50; 600/300; 600/316; 600/446

(58) Field of Classification Search ........................ None
See application file for complete search history.

(56) References Cited

U.S. PATENT DOCUMENTS

| | | | |
|---|---|---|---|
| 5,089,229 A * | 2/1992 | Heidt et al. .................... | 422/64 |
| 5,281,395 A | 1/1994 | Markart et al. | |
| 5,380,487 A | 1/1995 | Choperena et al. | |
| 5,406,263 A * | 4/1995 | Tuttle ...................... | 340/572.1 |
| 5,443,790 A | 8/1995 | Coeurveille et al. | |
| 5,578,269 A | 11/1996 | Yarenko et al. | |
| 5,670,375 A | 9/1997 | Seaton et al. | |
| 5,682,143 A * | 10/1997 | Brady et al. ............. | 340/572.7 |
| 5,902,549 A * | 5/1999 | Mimura et al. ................ | 422/65 |
| 5,980,830 A | 11/1999 | Savage et al. | |
| 6,146,510 A | 11/2000 | Leader et al. | |
| 6,259,562 B1 | 7/2001 | Shie et al. | |

(Continued)

OTHER PUBLICATIONS

International Search Report and Written Opinion, PCT/US07/09878, Sep. 16, 2008.

*Primary Examiner*—Jill Warden
*Assistant Examiner*—Neil Turk
(74) *Attorney, Agent, or Firm*—Antonelli, Terry, Stout & Kraus, LLP.

(57) ABSTRACT

A bodily fluid analyzer, system and method for programming the same includes a sensor for sensing at least one analyte in a patient; a display; a data reader unit for reading information from a data storage unit that contains stored information concerning a particular drug being taken by or course of treatment for the patient; and a processor for setting the at least one threshold value for at least one analyte to be sensed by the sensing unit based on the information read by the data reader from the data storage unit, for processing the information concerning the analyte and for sending the processed information to the display, wherein the threshold value is associated with the particular drug taken by or course of treatment for the patient, the threshold value being one beyond which the display will display an alert.

19 Claims, 2 Drawing Sheets

U.S. PATENT DOCUMENTS

| | | |
|---|---|---|
| 6,302,855 B1 | 10/2001 | Lav et al. |
| 6,663,003 B2 | 12/2003 | Johnson et al. |
| 6,845,327 B2 | 1/2005 | Lauks |
| 7,027,849 B2 | 4/2006 | Al-Ali |
| 2002/0128864 A1* | 9/2002 | Maus et al. .................... 705/2 |
| 2003/0141981 A1* | 7/2003 | Bui et al. .................... 340/608 |
| 2003/0208113 A1* | 11/2003 | Mault et al. ................. 600/316 |
| 2004/0106859 A1 | 6/2004 | Say et al. |
| 2005/0100937 A1 | 5/2005 | Holmes |
| 2006/0062852 A1 | 3/2006 | Holmes |

* cited by examiner

BODILY FLUID ANALYZER, AND SYSTEM INCLUDING SAME AND METHOD FOR PROGRAMMING SAME

CROSS-REFERENCE TO RELATED APPLICATION

This application is a nonprovisional application claiming the benefit of the filing date of U.S. application Ser. No. 60/794,117, filed Apr. 24, 2006, the contents of which are incorporated herein by reference.

TECHNICAL FIELD

Devices for measuring bodily fluid analytes, especially blood analytes such as glucose, are known. Recently, attempts have been made to provide such devices for home use.

Devices for measuring bodily fluid analytes are described in U.S. Pat. Nos. 5,980,830, 6,146,510, 6,259,562, 6,302,855, 6,845,327 and 7,027,849 and United States Patent Application Publication Nos. 2005/0100937A1 and 2006/0062852A1.

United States Patent Publication No. 2004/0106859 A1 to Say et al discloses an analyte monitoring device and methods of use, and discloses that the device may include an optional alarm system that warns the patient of a potentially detrimental condition of the analyte. The alarm system is triggered when the data from the processing circuit reaches or exceeds a threshold value. The analyte monitor device may be configured so that the threshold levels may be programmable by the patient and/or a medical professional. In addition, it is disclosed that, in some embodiments of the invention, the device may include a transmitter configured to transmit data to another receiver/display unit or some other receiver. As an example, it is disclosed that a receiver/display unit may transmit data to a computer in the patient's home or at a doctor's office. Moreover, the transmitter or a separate transmitter may direct a transmission to another unit or to a telephone or other communications device that alerts a doctor or other individual when an alarm is activated and/or if, after a predetermined time period, an activated alarm has not been deactivated, suggesting that the patient may require assistance. In some embodiments, the receiver/display unit is capable of one-way or two-way paging and/or is coupled to a telephone line to send and/or receive messages from another, such as a health professional monitoring the patient.

A biomonitoring and informatics system is under development by Theranos, Inc. and is described on the company website as follows.

Theranos is preparing to launch the first personalized biomonitoring and informatics system to monitor the effects of prescription medicines. Theranos devices enable healthcare professionals and pharmaceutical companies to track patients' individual responses to prescribed medicines, painlessly and in real time, throughout the course of treatment.

Based on a proprietary process, the Theranos handheld monitors simultaneously detect changes in the levels of biochemical markers directly induced by the drug, and then wirelessly communicate results to medical personnel through a bioinformatics server.

The Theranos platform consists of a Reader and disposable cartridges that analyze a specific prescription medicine. The Reader automatically transmits analysis data to the HIPAA-compliant Theranos database, which rigorously protects patient identity information while making available to healthcare professionals detailed, high-level and real-time information.

The highly portable, easy-to-use Reader can be used with all Theranos disposable cartridges, meaning that individuals can use the same Reader to gather and transmit information on any number of targeted prescription medicines.

However, applicants have found that what is still needed is a device, especially a home use device, and method that can make programming of such a device simple and specific to a particular drug or course of treatment.

DISCLOSURE OF INVENTION

The present invention relates to a method for programming a bodily fluid analyzer, including providing a data storage unit containing stored information concerning a particular drug being or to be taken by the patient or course of treatment for the patient; reading the stored information stored on the data storage unit into a data reader associated with a bodily fluid analyzer; setting at least one threshold value for at least one analyte to be sensed by the bodily fluid analyzer based on the information read by the data reader from the data storage unit, wherein the threshold value is associated with the particular drug being or to be taken by the patient or course of treatment for the patient, the threshold value being one beyond which the display will display an alert; sensing the analyte; and displaying an alert if the sensed analyte level is beyond the threshold value.

The present invention also relates to a bodily fluid analyzer including a sensor for sensing at least one bodily fluid analyte in a patient; a display for displaying processed information concerning the sensed analyte; a data reader unit for reading information from a data storage unit, the data storage unit containing stored information concerning a particular drug being or to be taken by the patient or course of treatment for the patient; and a processor for setting the at least one threshold value for at least one analyte to be sensed by the sensing unit based on the information read by the data reader from the data storage unit, for processing the information concerning the analyte and for sending the processed information to the display, wherein the threshold value is associated with the particular drug being or to be taken by the patient or course of treatment for the patient, the threshold value being one beyond which the display will display an alert.

The present invention also relates to a system for monitoring a patient, including such a bodily fluid analyzer and a data storage unit that may be provided with a drug container.

The bodily fluid may be blood, urine, etc.

MODES FOR CARRYING OUT THE INVENTION

Figure 1:
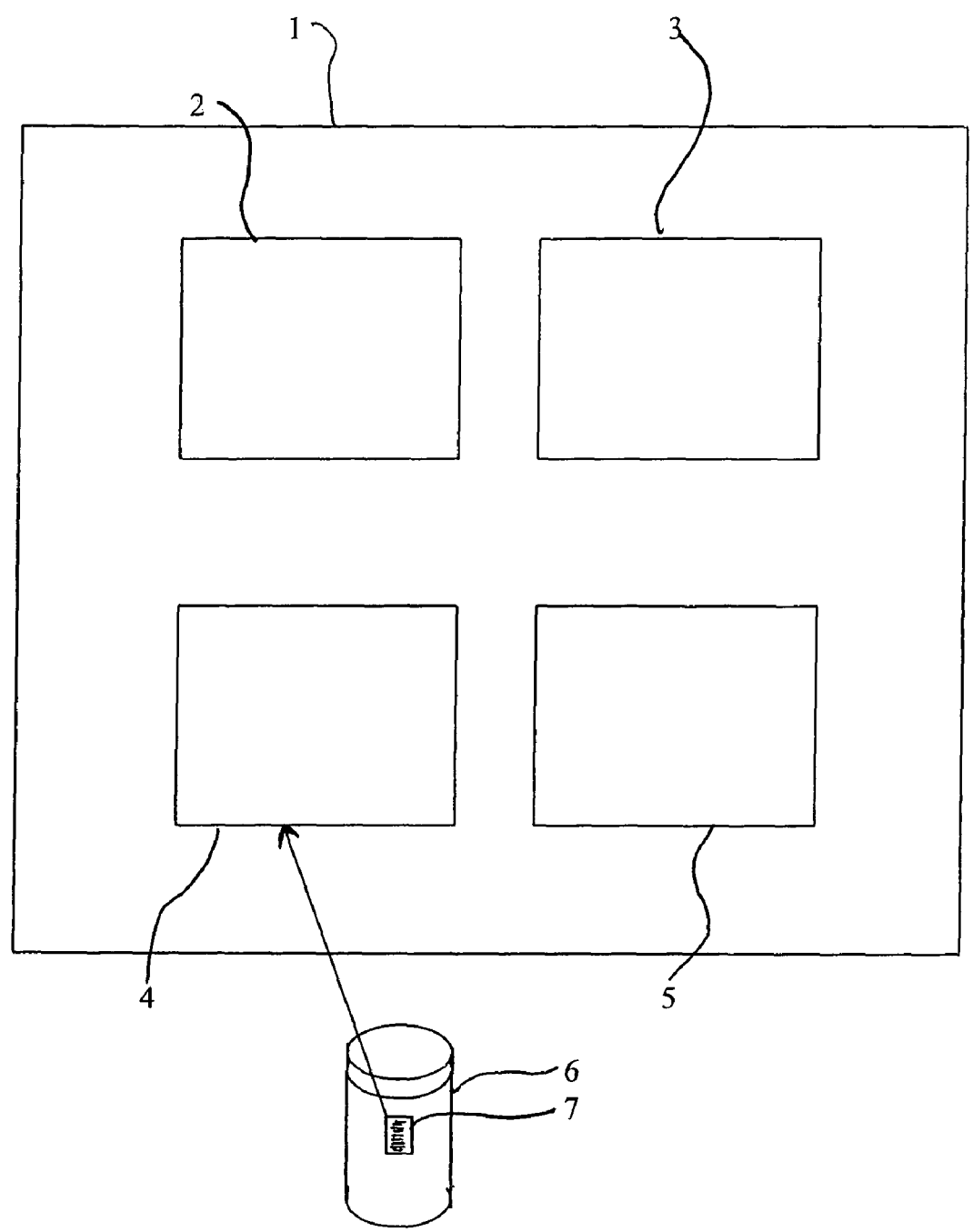
FIG. 1 is a schematic view of the bodily fluid analyzer and system of the present invention.

Devices for measuring bodily fluid analytes are described in U.S. Pat. Nos. 5,980,830, 6,146,510, 6,259,562, 6,302,855, 6,845,327 and 7,027,849 and United States Patent Application Publication Nos. 2005/0100937A1 and 2006/0062852A1, the content of each of which (including the drawings thereof) is incorporated herein in its entirety. The bodily fluid analyzer of the present invention includes a sensor for sensing at least one analyte in a patient; a display for displaying processed information concerning the sensed analyte; and a processor for processing the information concerning the analyte and for sending the processed information to the display. The sensor, the display and this basic aspect of the processor (processing the information concerning the analyte and for sending the processed information to the display) can be of the type described in U.S. Pat. Nos. 5,980,830, 6,146, 510, 6,259,562, 6,302,855, 6,845,327 and 7,027,849 and United States Patent Application Publication Nos. 2005/0100937A1 and 2006/0062852A1. The present invention is an improvement of the devices, systems and methods described in these patents and patent application publications. For example, the present invention provides a simple way for users to program such devices, e.g., the device of United States Patent Application Publication No. 2006/0062852A1 by transmitting what to check and appropriate parameters to use.

The present invention modifies such devices by, inter alia, including a data reader unit for reading information from a data storage unit, the data storage unit containing stored information concerning a particular drug being or to be taken by the patient or course of treatment for the patient; and a processor for setting the at least one threshold value for at least one analyte to be sensed by the sensing unit based on the information read by the data reader from the data storage unit, for processing the information concerning the analyte and for sending the processed information to the display, wherein the threshold value is associated with the particular drug being or to be taken by the patient or course of treatment for the patient, the threshold value being one beyond which the display will display an alert.

The data storage unit may be provided with a drug container or otherwise supplied by a caregiver to the patient. For example, the data storage unit can be a bar code and the data reader can be a bar code reader; the data storage unit can be a radio frequency identification tag and the data reader a radio frequency receiver; the data storage unit can be a magnetic stripe and the data reader a magnetic stripe reader. Thus, the patient can merely scan the bar code, move the radio frequency identification tag near the reader or swipe the magnetic stripe so that the data associated with the particular drug being or to be taken by the patient or course of treatment for the patient is read in a simple and foolproof manner.

The data can be transmitted wirelessly from the data storage unit to the data reader by any means known in the field of wireless data transmission, e.g., Bluetooth or Wi-Fi. At the same time the data is being transmitted to the data reader, it may be transmitted wirelessly (e.g., by Wi-Fi or Bluetooth) to the user's computer. The user's computer may contain a software application allowing the user to maintain a database or list of medications the user is taking.

When using a radio frequency identification tag, the tag can be activated upon opening of the medication container. Since such tags have a finite life, activating the tag upon opening of the container will ensure that the tag is active during the monitoring.

A schematic view of one example of the bodily fluid analyzer and system of the present invention is shown in FIG. 1. The system includes a bodily fluid analyzer 1 includes a sensor 2 for sensing at least one analyte in a patient, a display 3 for displaying processed information concerning the sensed analyte, a data reader unit 4 for reading information, and a processor 5 for setting the at least one threshold value for at least one analyte to be sensed by the sensing unit 2 based on the information read by the data reader 4, for processing the information concerning the analyte and for sending the processed information to the display 3, wherein the threshold value is associated with the particular drug being or to be taken by the patient or course of treatment for the patient, the threshold value being one beyond which the display 3 will display an alert. A drug container 6 includes a data storage unit 7. The data reader unit 4 reads information from a data storage unit 7, the data storage unit 7 containing stored information concerning a particular drug being or to be taken by the patient or course of treatment for the patient.

The data stored on the data storage unit may be preset parameters to be monitored, parameters that are important for the particular drug or course of treatment. Alternatively, the data stored on the data storage unit may store parameters that are set by the prescribing physician specifically for that particular patient or by the prescribing physician or drug company for a class of patients (e.g., elderly). Alternatively, if, e.g., if the data storage unit stores preset parameters, the device may contain an input unit (physically connected or remotely connected) so that the physician can narrow or widen the parameters to meet the special physiology of a particular patient. For example, the physician may well want a wider creatinine tolerance in an 80 year old than in a 20 year old. The processor could also calculate, e.g., creatinine clearance or other analyte limits from the patient's age, height, weight and measured serum creatinine.

For example, it is known that Captopril™ or Lisinopril™ can lead to elevated potassium (K) levels. Therefore, according to the present invention, the data storage unit may contain preset parameters regarding K levels to be monitored, e.g., the data storage unit may be used to program the device to set alarms when the K level is outside the range of 3.5-5.0 Meq/L. Alternatively, the data stored on the data storage unit may contain parameters that are set by the prescribing physician specifically for that particular patient or by the prescribing physician or drug company for a class of patients (e.g., elderly), e.g., the prescribing physician may want to store data to bump the preset K range up to 5.5 if the patient chronically ran high.

For example, it is known that Furosemide™ can lead to elevated creatinine or low K levels. The data storage unit may be used to program the device to set alarms when the K level is outside the range of 3.5-5.0 Meq/L or the creatinine 0.6-1.2 Mg/dL. However, if the patient's if the baseline creatinine is 1.6, the physician could change the creatinine range to 1.2 to 2.0. This can be done by having the data stored on the data storage unit set by the prescribing physician specifically for that particular patient or, alternatively, the device may contain an input unit (physically connected or remotely connected) so that the physician can narrow or widen the parameters to meet the special physiology of a particular patient.

For example, the data storage unit associated with a drug container containing Lipitor™ can set ALT>150 iu/L as an upper limit (normal is 48). The data storage unit associated with a drug container containing Metformin™ can set creatine clearance<60 ml/min.

For example, it is known that a normal level of potassium is 3.5-5 meq/L; hypokalemia is defined when potassium level is below 3.5 meq/L. The normal level for sodium (Na) is 136-145 meq/L; hyponatremia occurs when sodium level is below 130 meq/L. Prescription of a thiazide diuretic in primary care can be associated with high frequency of hyponatrimia and hypokalemia. The risk of hyponatremia, especially in the elderly, should be considered and monitored. Therefore, a drug container containing a thiazide diuretic would have a data storage unit on having data stored with preset parameters from which the processor can set at least one threshold value for K or Na, e.g., set alarms if the K level is below 3.5 meq/L or the Na level is below 130 meq/L.

Figure 2:
FIGS. 2-6 show examples of bar codes encoded for use in the present invention.
Figure 3:
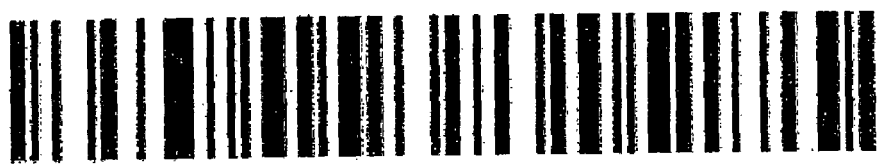
Figure 4:
Figure 5:
Figure 6:

FIGS. 2-6 show examples of bar codes encoded for use in the present invention. The bar codes were encoded in a manner known in the bar code art. FIG. 2 shows a bar code encoded for potassium and sodium levels, in this case potassium 1.5-4 and sodium 2-10 encoded as a Code 3 of 9 full ASCII barcode. FIG. 3 shows a bar code encoded for the string "D×10ch20" as a Code 128 barcode. FIG. 4 shows a bar code encoded for the string "D×10 PE20" as a Code 3 of 9 full ASCII barcode. FIG. 5 shows a bar code encoded for the string "BNP>100" as a Code 3 of 9 full ASCII barcode for brain natruiretic peptide (BNP) where 100 pg/mL=mild heart failure pt. on Lisinopril etc. and >600 associates with moderate failure. FIG. 6 shows a bar code encoded for the string "K3.5-5.3" as a Code 3 of 9 full ASCII barcode for potassium (3.5-5.3 meq/L) low endstop for Lasix and high endstop for ace-inhibitors. FIGS. 2-6 are examples only. Other data of the types mentioned above can be encoded on bar codes or can be stored in other data storage units, e.g., radio frequency identification tags, magnetic stripes, etc.

If the analyzer is of the type that uses disposable cartridges, the data storage unit may contain information as to what a particular drug is and the processor processes this information to display it on the display so that the patient does not put the wrong cartridge (i.e., a cartridge for the wrong drug) in the analyzer. The processor could also give an alert if the wrong cartridge is accidentally place in the analyzer.

The present invention enables the linkage of transmission to the analyzer Bios system. This may be done according to the present invention by the standard drug container having more information on it to communicate with the analyzer as to what is to be measured. The present invention has unexpectedly advantageous results as compared to known systems. For example, with respect to the analyzer described by Theranos, the analyzer is claimed to be module specific; however, if the patient were responsible for placing the proper module in the analyzer, this would be a compliance nightmare. The present invention will enable a huge advance in medical care by simplifying the home analysis of fluids for monitoring health as well as for the monitoring of a specific drug (e.g., a drug company clinical trial). The present invention will enable the pill container via a reader to give full instruction to the analyzer as to what the fluid is and what parameter is to be measured. This presupposes that future drug containers will contain this information, e.g., on a data storage unit, or that the care provider otherwise gives the information to the patient. As time gains, the system can be further advanced by the additional data contained on the container and read by the reader of wider or narrower or higher or lower values of a particular analyte for a particular patient.

The device and system of Theranos may be used for clinical trials. However, the very basis of clinical trials is that, through labeling known only to the pharmaceutical company, some patients end up with the drug that is the subject of the trial and others with placebo. Using the method, system and device of the present invention for informing, through bar code, radio tag, Bluetooth or other technology, the parameter to be measured on the patient results in not giving the investigator knowledge of which is drug and which is placebo and what is measured so that the investigator cannot bias the outcome by other means such as diet, other drugs etc.

While the present invention is particularly described with respect to blood analyzers, those skilled in the art would understand, from the foregoing description, that the invention could be used with analyzers of other bodily fluids. The data storage unit may contain information the processor can use to determine the fluid to be analyzed.

The data storage unit may contain a universal analyzer code by which the physician can prescribe the code on a container or directly to a reader—not simply of the fluid analyzed and the specific analyte, but the range of normal as well. For example, a theoretical code BK1 or BK2 or BK3 will mean Blood-Potassium and range of normal schema 1 or 2 or 3.

In the future, the drug itself may contain the information read through its individual package or through a microchip in the dosage form itself.

We claim:

1. A method for programming a bodily fluid analyzer, comprising:
    selecting by a prescribing physician or a drug company at least one threshold value of at least one analyte to be sensed by the bodily fluid analyzer, the at least one threshold value of the at least one analyte being associated with a particular drug being or to be taken by the patient or course of treatment for the patient
    providing a data storage unit separately from the bodily fluid analyzer and containing stored information including the at least one threshold value of at least one analyte to be sensed by the bodily fluid analyzer selected by the prescribing physician or the drug company;
    reading the stored information stored on the data storage unit into a data reader associated with a bodily fluid analyzer;
    setting the bodily fluid analyzer with the at least one threshold value for the at least one analyte to be sensed by the bodily fluid analyzer with the information read by the data reader from the data storage unit, wherein the at least one threshold value is a value such that a sensed analyte level beyond the value will cause the display to display an alert;
    sensing the analyte level; and
    displaying an alert if the sensed analyte level is beyond the threshold value.

2. The method according to claim 1, wherein the data storage unit is provided with a drug container.

3. The method according to claim 2, wherein the data reader is a bar code reader and the data storage unit is a bar code.

4. The method according to claim 2, wherein the data reader is a radio frequency receiver and the data storage unit is a radio frequency identification tag.

5. The method according to claim 4, wherein the drug is provided in a closed container and the method further comprises opening the container and activating the radio frequency identification tag upon opening of the container.

6. The method according to claim 2, wherein the data reader is a magnetic stripe reader and the data storage unit is a magnetic stripe.

7. The method according to claim 1, wherein the at least one threshold value of the at least one analyte to be sensed by the bodily fluid analyzer is selected by a prescribing physician for the patient or for a class of patients.

8. The method according to claim 1, wherein the at least one threshold value of the at least one analyte to be sensed by the bodily fluid analyzer is selected by a drug company for the patient or for a class of patients.

9. A system for monitoring a patient, comprising a bodily fluid analyzer and a data storage unit provided seperately from the bodily fluid analyzer and containing stored information set by a prescribing physician or a drug company and including at least one threshold value of at least one analyte to be sensed by the bodily fluid analyzer, the at least one threshold value of the at least one analyte being associated with a particular drug being or to be taken by the patient or course of treatment for the patient, wherein the bodily fluid analyzer comprises:
- a sensor for sensing at least one analyte in a patient;
- a display for displaying processed information concerning the sensed analyte;
- a data reader unit for reading information from the data storage unit; and
- a processor configured for setting the bodily fluid analyzer with the at least one threshold value for the at least one analyte to be sensed in accordance with the information read by the data reader from the data storage unit, and configured for processing the information concerning the analyte and configured for sending the processed information to the display, wherein the at least one threshold value is a value such that a sensed analyte level beyond the value will cause the display to display an alert.

10. The system according to claim 9, wherein the data reader unit is a bar code reader.

11. The system according to claim 9, wherein the data reader unit is a radio frequency receiver.

12. The system according to claim 9, wherein the data reader unit is a magnetic stripe reader.

13. The system according to claim 9, wherein the display is provided proximate the sensor.

14. The system according to claim 9, wherein the data storage unit is associated with a drug container.

15. The system according to claim 9, wherein the data reader is a bar code reader and the data storage unit is a bar code.

16. The system according to claim 9, wherein the data reader is a radio frequency receiver and the data storage unit is a radio frequency identification tag.

17. The system according to claim 9, wherein the data reader is a magnetic stripe reader and the data storage unit is a magnetic stripe.

18. The system according to claim 9, wherein the at least one threshold value of the at least one analyte to be sensed by the bodily fluid analyzer is selected by a prescribing physician for the patient or for a class of patients.

19. The system according to claim 9, wherein the at least one threshold value of the at least one analyte to be sensed by the bodily fluid analyzer is selected by a drug company for the patient or for a class of patients.

* * * * *